US007255877B2

(12) United States Patent
Parikh

(10) Patent No.: US 7,255,877 B2
(45) Date of Patent: *Aug. 14, 2007

(54) FENOFIBRATE MICROPARTICLES

(75) Inventor: Indu Parikh, Verdun (CA)

(73) Assignee: Jagotec AG, Muttenz (CH)

( * ) Notice: Subject to any disclaimer, the term of this patent is extended or adjusted under 35 U.S.C. 154(b) by 0 days.

This patent is subject to a terminal disclaimer.

(21) Appl. No.: 09/282,471

(22) Filed: Mar. 31, 1999

(65) Prior Publication Data

US 2002/0119199 A1    Aug. 29, 2002

Related U.S. Application Data

(63) Continuation-in-part of application No. 09/218,080, filed on Dec. 22, 1998, now Pat. No. 6,228,399, which is a continuation-in-part of application No. 08/701,483, filed on Aug. 22, 1996, now abandoned.

(51) Int. Cl.
*A61K 9/16* (2006.01)
(52) U.S. Cl. .............. 424/489; 424/490; 424/497; 424/501; 515/557
(58) Field of Classification Search ............... 424/451, 424/464, 489–502
See application file for complete search history.

(56) References Cited

U.S. PATENT DOCUMENTS

| | | | |
|---|---|---|---|
| 2,803,582 A | 8/1957 | Cherney | |
| 3,137,631 A | 6/1964 | Soloway | |
| 3,216,897 A | 11/1965 | Krantz | |
| 3,274,063 A | 9/1966 | Nieper et al. | |
| 3,594,476 A | 7/1971 | Merrill | |
| 3,715,432 A | 2/1973 | Merrill | |
| 3,755,557 A | 8/1973 | Jacobs | |
| 3,794,476 A | 2/1974 | Michalik et al. | |
| 3,937,668 A | 2/1976 | Zolle | |
| 3,960,757 A | 6/1976 | Morishita et al. | |
| 3,965,255 A | 6/1976 | Bloch et al. | |
| 4,016,100 A | 4/1977 | Suzuki et al. | |
| 4,053,585 A | 10/1977 | Allison et al. | |
| 4,073,943 A | 2/1978 | Wretlind et al. | |
| 4,078,052 A | 3/1978 | Papahadjopoulos | |
| 4,089,801 A | 5/1978 | Schneider | |
| 4,102,806 A | 7/1978 | Kondo et al. | |
| 4,107,288 A | 8/1978 | Oppenheim et al. | |
| 4,133,874 A | 1/1979 | Miller et al. | |
| 4,145,410 A | 3/1979 | Sears | |
| 4,147,767 A | 4/1979 | Yapel, Jr. | |
| 4,186,183 A | 1/1980 | Steck et al. | |
| 4,219,548 A | 8/1980 | Reller | |
| 4,235,871 A | 11/1980 | Papahadjopoulos et al. | |
| 4,241,046 A | 12/1980 | Papahadjopoulos et al. | |
| 4,271,196 A | 6/1981 | Schmidt | |
| 4,298,594 A | 11/1981 | Sears et al. | |
| 4,302,459 A | 11/1981 | Steck et al. | |
| 4,308,166 A | 12/1981 | Marchetti et al. | |
| 4,309,421 A | 1/1982 | Ghyczy et al. | |
| 4,316,884 A | 2/1982 | Alam et al. | |
| 4,320,121 A | 3/1982 | Sears | |
| 4,325,871 A | 4/1982 | Sasaki et al. | |
| 4,328,222 A | 5/1982 | Schmidt | |
| 4,329,332 A | 5/1982 | Couvreur et al. | |
| 4,331,654 A | 5/1982 | Morris | |
| 4,332,795 A | 6/1982 | Ghyczy et al. | |
| 4,332,796 A | 6/1982 | Los | |
| 4,340,594 A | 7/1982 | Mizushima et al. | |
| 4,345,588 A | 8/1982 | Widder et al. | |
| 4,351,831 A | 9/1982 | Growdon et al. | |
| 4,356,167 A | 10/1982 | Kelly | |
| 4,369,182 A | 1/1983 | Ghyczy et al. | |
| 4,371,516 A | 2/1983 | Gregory et al. | |
| 4,378,354 A | 3/1983 | Ghyczy et al. | |
| 4,394,372 A | 7/1983 | Taylor | |
| 4,397,846 A | 8/1983 | Weiner et al. | |
| 4,411,894 A | 10/1983 | Schrank et al. | |
| 4,411,933 A | 10/1983 | Samejima et al. | 427/213.3 |
| 4,421,747 A | 12/1983 | Ghyczy et al. | |
| 4,427,649 A | 1/1984 | Dingle et al. | |
| 4,432,975 A | 2/1984 | Libby | |
| 4,448,765 A | 5/1984 | Ash et al. | |
| 4,483,847 A | 11/1984 | Augart | |
| 4,485,054 A | 11/1984 | Mezei et al. | |
| 4,492,720 A | 1/1985 | Mosier | |
| 4,515,736 A | 5/1985 | Deamer | |
| 4,529,561 A | 7/1985 | Hunt et al. | |

(Continued)

FOREIGN PATENT DOCUMENTS

DE          2 513 797          10/1975

(Continued)

OTHER PUBLICATIONS

International Search Report (PCT/US97/04794).

(Continued)

*Primary Examiner*—Gollamudi S. Kishore
(74) *Attorney, Agent, or Firm*—Ivor R. Elrifi, Esq.; Naomi S. Biswas, Esq.; Mintz, Levin

(57) ABSTRACT

Fenofibrate microparticles are prepared using a combination of surface modifiers with a phospholipid. Particle size growth and stability are controlled while significantly smaller sized fenofibrate particles are produced.

29 Claims, No Drawings

U.S. PATENT DOCUMENTS

| | | | |
|---|---|---|---|
| 4,532,089 A | 7/1985 | MacDonald | |
| 4,610,868 A | 9/1986 | Fountain et al. | |
| 4,613,505 A | 9/1986 | Mizushima et al. | |
| 4,622,219 A | 11/1986 | Haynes | |
| 4,629,626 A | 12/1986 | Miyata et al. | |
| RE32,393 E | 4/1987 | Wretlind et al. | |
| 4,675,236 A | 6/1987 | Ohkawara et al. | |
| 4,687,762 A | 8/1987 | Fukushima et al. | |
| 4,725,442 A | 2/1988 | Haynes | 424/490 |
| 4,752,442 A | 6/1988 | Asada et al. | |
| 4,756,910 A | 7/1988 | Yagi et al. | |
| 4,758,598 A | 7/1988 | Gregory | |
| 4,761,288 A | 8/1988 | Mezei | |
| 4,762,720 A | 8/1988 | Jizomoto | |
| 4,766,046 A | 8/1988 | Abra et al. | |
| 4,776,991 A | 10/1988 | Farmer et al. | |
| 4,800,079 A | 1/1989 | Boyer | |
| 4,801,455 A | 1/1989 | List et al. | |
| 4,803,070 A | 2/1989 | Cantrell et al. | |
| 4,806,350 A | 2/1989 | Gerber | |
| 4,806,352 A | 2/1989 | Cantrell | |
| 4,826,687 A | 5/1989 | Nerome et al. | |
| 4,839,111 A | 6/1989 | Huang | |
| 4,895,726 A | 1/1990 | Curtet et al. | |
| 4,961,890 A | 10/1990 | Boyer | |
| 4,963,367 A * | 10/1990 | Ecanow | 424/485 |
| 4,973,465 A | 11/1990 | Baurain et al. | |
| 4,990,337 A | 2/1991 | Kurihara et al. | 424/427 |
| 5,030,453 A | 7/1991 | Lenk et al. | |
| 5,091,187 A * | 2/1992 | Haynes | 424/450 |
| 5,091,188 A | 2/1992 | Haynes | 424/450 |
| 5,100,591 A | 3/1992 | Leclef et al. | |
| 5,145,684 A | 9/1992 | Liversidge et al. | |
| 5,164,380 A | 11/1992 | Carli et al. | |
| 5,178,878 A | 1/1993 | Wehling et al. | |
| 5,179,079 A | 1/1993 | Hansen et al. | |
| 5,217,707 A | 6/1993 | Szabo et al. | |
| 5,246,707 A | 9/1993 | Haynes | |
| 5,272,137 A | 12/1993 | Blasé et al. | |
| 5,298,262 A | 3/1994 | Na et al. | |
| 5,302,401 A | 4/1994 | Liversidge et al. | |
| 5,304,564 A | 4/1994 | Tsuboi et al. | |
| 5,326,552 A | 7/1994 | Na et al. | 424/4 |
| 5,336,507 A | 8/1994 | Na et al. | |
| 5,340,564 A | 8/1994 | Illig et al. | |
| 5,346,702 A | 9/1994 | Na et al. | |
| 5,352,459 A | 10/1994 | Hollister et al. | |
| 5,360,593 A | 11/1994 | Bapatia | |
| 5,364,633 A | 11/1994 | Hill et al. | 424/450 |
| 5,389,377 A | 2/1995 | Chagnon et al. | 424/450 |
| 5,399,363 A | 3/1995 | Liversidge et al. | |
| 5,447,710 A | 9/1995 | Na et al. | 424/9.455 |
| 5,470,583 A | 11/1995 | Na et al. | |
| 5,510,118 A | 4/1996 | Bosch et al. | |
| 5,527,537 A | 6/1996 | Dietl | 424/450 |
| 5,545,628 A | 8/1996 | Deboeck et al. | |
| RE35,338 E | 9/1996 | Haynes | |
| 5,552,160 A | 9/1996 | Liversidge et al. | |
| 5,560,931 A | 10/1996 | Eickhoff et al. | |
| 5,569,448 A | 10/1996 | Wong et al. | |
| 5,571,536 A | 11/1996 | Eickhoff et al. | |
| 5,576,016 A | 11/1996 | Amselem et al. | |
| 5,578,325 A | 11/1996 | Domb et al. | |
| 5,589,455 A | 12/1996 | Woo | 514/11 |
| 5,603,951 A | 2/1997 | Woo | 424/455 |
| 5,631,023 A | 5/1997 | Kearney et al. | |
| 5,637,625 A | 6/1997 | Haynes | |
| 5,639,474 A | 6/1997 | Woo | 424/452 |
| 5,645,856 A | 7/1997 | Lacy et al. | |
| 5,656,289 A | 8/1997 | Cho et al. | |
| 5,660,854 A | 8/1997 | Haynes et al. | |
| 5,660,858 A | 8/1997 | Parikh et al. | |
| 5,662,932 A | 9/1997 | Amselem et al. | |
| 5,663,198 A | 9/1997 | Reul et al. | |
| 5,676,928 A | 10/1997 | Klaveness et al. | |
| 5,776,491 A | 7/1998 | Allen, Jr. et al. | |
| 5,776,495 A * | 7/1998 | Duclos et al. | 424/455 |
| 5,827,822 A | 10/1998 | Floc'h et al. | |
| 5,834,025 A | 11/1998 | de Garavilla et al. | |
| 5,851,275 A | 12/1998 | Amidon et al. | |
| 5,858,398 A | 1/1999 | Cho | |
| 5,858,410 A | 1/1999 | Muller et al. | |
| 5,922,355 A * | 7/1999 | Parikh et al. | 424/489 |
| 5,932,243 A | 8/1999 | Fricker et al. | |
| 5,972,366 A | 10/1999 | Haynes et al. | |
| 5,976,577 A | 11/1999 | Green et al. | |
| 6,045,829 A | 4/2000 | Liversidge et al. | |
| 6,074,670 A | 6/2000 | Stamm et al. | 424/462 |
| 6,228,399 B1 * | 5/2001 | Parikh et al. | 424/489 |
| 6,267,989 B1 | 7/2001 | Liversidge et al. | |
| 6,270,806 B1 | 8/2001 | Liversidge et al. | |
| 6,277,405 B1 | 8/2001 | Stamm et al. | 424/462 |
| 6,337,092 B1 | 1/2002 | Khan et al. | |
| 6,375,986 B1 | 4/2002 | Ryde et al. | 424/489 |
| 6,387,409 B1 | 5/2002 | Khan et al. | |
| 6,589,552 B2 | 7/2003 | Stamm et al. | 424/457 |
| 6,652,881 B2 | 11/2003 | Stamm et al. | 424/462 |

FOREIGN PATENT DOCUMENTS

| | | |
|---|---|---|
| DE | 2 938 807 | 11/1980 |
| DE | 3 421 468 | 12/1985 |
| DE | 34 21 468 A1 | 12/1985 |
| DE | 4 440 337 | 5/1996 |
| EP | 0 052 322 | 5/1982 |
| EP | 0 193208 | 9/1986 |
| EP | 0 272 091 | 6/1988 |
| EP | 0 330 532 | 8/1989 |
| EP | 0 391 369 | 10/1990 |
| EP | 0 418 153 | 3/1991 |
| EP | 0 456 670 | 11/1991 |
| EP | 0 456 764 | 11/1991 |
| EP | 0 499 299 | 8/1992 |
| EP | 0 570 829 | 5/1993 |
| EP | 0 570 829 | 11/1993 |
| EP | 0 580 690 | 2/1994 |
| EP | 0 601 618 A2 | 6/1994 |
| EP | 0 602 700 A2 | 6/1994 |
| EP | 0 605 497 | 3/1996 |
| EP | 0 724 877 | 8/1996 |
| EP | 0 724 877 A1 | 8/1996 |
| EP | 0 757 911 A1 | 2/1997 |
| FR | 2 617 047 | 12/1988 |
| FR | 2 617 047 | 3/1996 |
| GB | 1 527 638 | 10/1978 |
| GB | 2046094 | 9/1986 |
| HU | 211 580 B | 6/1995 |
| JP | 56167616 | 5/1980 |
| JP | 1502590 | 11/1980 |
| JP | 55141407 | 11/1980 |
| JP | 60208910 | 11/1980 |
| JP | 63233915 | 10/1985 |
| JP | 63502117 | 9/1986 |
| WO | WO 8500011 | 1/1985 |
| WO | WO 8704592 | 8/1987 |
| WO | WO 9104011 | 4/1991 |
| WO | WO 92/18105 | 10/1992 |
| WO | 94/20072 | 9/1994 |
| WO | 96/21439 | 7/1996 |
| WO | WO 96/21439 | 7/1996 |
| WO | WO 96/24332 | 8/1996 |
| WO | WO 97/14407 | 4/1997 |
| WO | WO 9807414 | 2/1998 |
| WO | WO 98/41239 | 9/1998 |

| WO | WO 99/29300 | 6/1999 |
| WO | WO 99/29316 | 6/1999 |
| WO | WO 99/49846 | 10/1999 |
| WO | WO 99/49848 | 10/1999 |
| WO | WO 9961001 | 12/1999 |
| WO | WO 00/10531 | 3/2000 |
| WO | WO 0030615 | 6/2000 |
| WO | WO 0030616 | 6/2000 |
| WO | WO 00/40219 | 7/2000 |
| WO | WO 00/41682 | 7/2000 |
| WO | WO 01/30372 | 5/2001 |

OTHER PUBLICATIONS

International Search Report (PCT/US 98/26075).
Lehninger Biochemistry The Molecular Basis of Cell Structure and Function 1970 Chapter 10.
Ross et al., "Aqueous Solutions of Surface-Active Solutes", *Collodial Systems and Interfaces*, © 1988, pp. 148-151.
Sande et al., "Antimicrobial Agents: Antifungal and Antiviral Agents", pp. 1219-1222, 1985.
Bittman, Robert, "Sterol-Polyene Antibiotic Complexation: Probe of Membrane Structure," *Lipids*, vol. 13, No. 10, pp. 686-691 (1978).
Mishra et al., "Scientifically Speaking: Novel Injectable Formulations of Water-Insoluble Drugs", *Controlled Release Newsletter*, vol. 17, Issue 2, (Jun. 2000), pp. 21-30.
Bangham et al., "Diffusion of Univalent Ions Across the Lamellae of Swollen Phospholipids", *J. Mol. Biol.* (1965) 13, pp. 238-252.
Huang et al., "Interaction of the N-terminus of Sterol Carrier Protein 2 with Membranes: Role of Membrane Curvature", *Biochem. J*, (1999) vol. 8, pp. 593-603.
Gregoriadis, Gregory, "The Carrier Potential of Liposomes in Biology and Medicine", *New Engl. J. Med.*, (1976) vol. 295, No. 13, pp. 704-710.
Cudd et al., "Liposomes Injected Intravenously into Mice Associate with Liver Mitochondria," *Biochem. Biophys Acta*, (1984) vol. 774, pp. 169-180.
Benz et al., "Electrical Capacity of Black Lipid Films and of Lipid Bilayers Made from Monolayers", *Biochem. Biophys. Acta*, (1975) vol. 394, pp. 323-334.
Goodman and Gillman's, "The Pharmacological Basis of Therapeutics," 7th Ed., *MacMillan Publishing Co.*, New York (1985) Chap. 15, p. 312.
Cherney, L.S., "Tetracaine Hydroiodide: A Long Lasting Local Anesthetic Agent for the Relief of Postoperative Pain", *Anesth. Analg.* (1963) vol. 42, No. 4, pp. 477-481.
Haynes et al., "Metal-Ligand Interactions in Organic Chemistry and Biochemistry", *B. Pullman and N. Goldblum* (eds.), part 2, (1977), pp. 189-212.
Haynes et al., "Ultra-Long Duration Local Anesthesia Produced by Injection of Lecithin-coated Methoxyflurane Microdroplets", *Anesthesiology* (1985) vol. 63, No. 5, pp. 490-499.
Haynes et al., "Ultra-Long Duration Local Anesthesia Produced by Intra-Dermal Injection of Lecithin-Coated Methoxyflurane Microdroplets", *Proceed. Intern. Symp. Control. Rel. Bioact. Mater.*, (1987) vol. 14, pp. 293-294.

Kirkpatrick et al., "Local Anesthetic Efficacy of Methoxyflurane Microdroplets in Man," *Anesthesiology* (1987) 67(3A): A254.
Gennaro et al., "Sustained-Release Drug Therapy," *Remington's Pharmaceutical Sciences*, 17th Ed., (1985), p. 1645.
"Getting Started", Man 0106, Issue 1.0, (Jan. 1996), *Malvern Instruments Ltd.*, England, pp. 7.1-7.7.
Chulia et al., Powder Technology and Pharmaceutical Processes, (1994), pp. 66-67.
Herbert A. Leiberman and Leon Lachman, Eds., *Pharmaceutical Dosage Forms*, Tablets, vol. 1, (1980), p. 13.
Miyajima, Koichiro, "Role of Saccharides for the Freeze-Thawing and Freeze-Drying of Liposome", *Advanced Drug Delivery Review*, vol. 24, (1997), pp. 151-159.
Buchmuller et al., "Cryopel: Ein neus Verfahren zum Pelletieren und Frosten Biologischer Substrate," *Gas Aktuell*, 35, 1(989), pp. 10-13.
Wu et al., "Pharmacokinetics of Methoxyflurane After Its Intra-Dermal Injection as Lecithin-Coated Microdroplets," *Journal of Controlled Release*, (1989), vol. 9, pp. 1-12.
Pace et al., "Novel Injectable Formulations of Insoluble Drugs", *Pharmaceutical Technology*, vol. 23, No. 3, (Mar. 1999), pp. 116-134.
Rompp's Chemie Lexikon, 2 Auftl., Bd. 1, (1950), Stichwort, "Emulsion".
Bergmann, Ludwig, *Der Ultraschall*, 5 Aufl., (1949), Stuttgart, S. 551-564, 672f.
Lehninger Biochemistry, "The Molecular Basis of Cell Structure and Function", (1970) Chapter 10.
Guzman et al., 1088 J. Pharm. Sci 82 (1993) No. 5 pp. 498-502 Formation and Characterization of Cyclosporine-Loaded Nanoparticles.
Napper, "Polymeric Stabilizations of Colloidal Dispersions", (1983).
Muller et al., Emulsions and Nanosuspension, Chap. 9 (1998) p. 163.
Lourenco et al., Int. J. of Pharm. 138 (1996), 1-12, "Steric stabilization of nanoparticles:size and surface properties".
Luckham Pestic. Sci., 1989, 25, 25-34, "The Physical Stability of Suspension Concentrates with Particular etc."
Calvor et al. Pharm. Dev. Tech., 3(3), 297-205, 1998, "Production of Microparticles by High Pressure etc."
[LSP4]La Fuma Polymery 1998 43 nr 2, 104-108, "The role of water-soluble polymers at the solid/liquid etc."
Siekmann et al. Pharm. Pharmacol Lett (1994) 3:225-228 "Melt-homogenized Solid Lipid Nanparticles Stabilized by the Non-ionic Surfactant Tyloxapol".
Muller et al., "Nanosuspensions for the I.V. Administration of Poorly Soluble Drugs-Stability During Sterilization and Long-Term Storage", Dept. of Pharmaceutics, Biopharmaceutics and Biotechnology, The Free University of Berlin, Kelchstraβe 31, D-12169 Berlin, Germany, 1995.
Zuidam et al. "Sterilization of Liposomes by Heat Treatment", Pharmaceutical Research, vol. 10, No. 11, 1993 pp. 1591-1596.

* cited by examiner

FENOFIBRATE MICROPARTICLES

This application is a continuation-in-part of application Ser. No. 09/218,080 filed Dec. 22, 1998 now U.S. Pat. No. 6,228,399 which is a continuation-in-part of application Ser. No. 08/701,483 filed Aug. 22, 1996, now abandoned. The disclosures of these applications are hereby incorporated by reference.

This invention relates to compositions and procedures that yield sub-micron and micron stable particles of fenofibrate. The compositions of this invention include combinations of natural or synthetic phospholipids, and one or more non-ionic, anionic or cationic surfactants coated or adhered onto the surfaces of the fenofibrate particles. The combination of phospholipids and surfactants allows the formation and stabilization of the sub-micron and micron size compound particles by modification of the surface and changes in hydrophilic, lipophilic and electrostatic interactions between particles.

BACKGROUND OF THE INVENTION

Fenofibrate is a prodrug that immediately after absorption is hydrolyzed by tissue and plasma esterases to its active major metabolite, fenofibric acid. Fenofibric acid is responsible for the pharmacological activity and its plasma half-life is about 20 hours. Fenofibrate is practically insoluble in water, it is poorly and variably absorbed and has to be taken with food.

Fenofibrate was first available in a pharmaceutical dosage form (Lipanthyl® also marketed under the trademarks Lipidil® and Lipantil®) consisting of a hard gelatin capsule containing fenofibrate, lactose, pregelatinized starch and magnesium stearate. After oral administration, during a meal, about 60% of the dose of this conventional form is effectively absorbed and found in the blood as fenofibric acid (Weil et al., The metabolism and disposition of 14C-fenofibrate in human volunteers, Drug. Metabol. Dispos. Biol. Fate. Chem., 18 (1990) 115-120).

Historically, in order to improve the intestinal absorption, another pharmaceutical dosage form was introduced (Lipanthyl® 67M and 200M, also marketed under the trademarks Lipidil Micro®, Lipantil®Micro and Tricor™). European Patent Application 330,532 and U.S. Pat. No. 4,895,726 disclose a fenofibrate composition in which the fenofibrate powder is co-micronized with a solid wetting agent. Sodium lauryl sulfate is described as the wetting agent of choice. The co-micronized powder so obtained is mixed with capsule filling excipients such as lactose, starch, cross-linked polyvinyl pyrrolidone and magnesium stearate. A study comparing this formulation (Lipidil Micro®) to the conventional form (Lipidil®) had shown statistically significant increase in bioavailability with the former.

However, co-micronization of the active drug fenofibrate with the wetting agent sodium lauryl sulfate, although necessary, has several drawbacks such as irritation of mucosal membranes of the gastrointestinal tract. In addition, micronization is a time consuming and costly operation and the filling of hard gelatin capsules with a micronized powder is a difficult operation when taking into account the possibility of weight variation due to poor homogeneity.

European Patent Application 724,877 describes fenofibrate powder co-micronized with a wetting agent in association with a vitamin E component (tocopherol and/or its organic acid ester) for treating or preventing disorders associated with lipoprotein oxidation.

U.S. Pat. No. 4,800,079 relates to a medicinal composition in the form of granules with controlled release of fenofibrate. Each granule includes an inert core, a layer based on fenofibrate and a protective layer. Fenofibrate is present in the form of crystalline microparticles of dimensions not greater than 30 μm.

U.S. Pat. No. 4,961,890 relates to a process for preparing a controlled release formulation containing fenofibrate in an intermediate layer in the form of crystalline microparticles (<30 μm in diameter) within a multilayer inert matrix.

U.S. Pat. No. 5,545,628 relates to a pharmaceutical composition for treating hyperlipidemia or hypercholesterolemia or both in a mammal, by providing an effective amount of each of fenofibrate and an excipient including one or more polyglycolyzed glycerides (generally mixtures of known monoesters, diesters and triesters of glycerols and known monoesters and diesters of polyethylene glycols). The polyglycolyzed glycerides may be obtained by partial trans-esterification of triglycerides with polyethylene glycol or by esterification of glycerol and polyethylene glycol with fatty acids.

European Patent Application 757,911 relates to a fenofibrate pharmaceutical dosage form in which fenofibrate is in solution in diethylene glycol monoethyl ether (EMDG) which is a non ionic surfactant.

Current technology for delivering insoluble drugs as described in U.S. Pat. Nos. 5,091,188; 5,091,187 and 4,725,442 focuses on (a) either coating small drug particles with natural or synthetic phospholipids or (b) dissolving the drug in a suitable lipophilic carrier and forming an emulsion stabilized with natural or semisynthetic phospholipids. One of the disadvantages of these formulations is that certain drug particles in suspension tend to grow in size over time because of the dissolution and reprecipitation phenomenon known as the Ostwald ripening or particle growth. The solvent becomes saturated with solute, the larger particles grow at the expense of smaller particles which preferentially solubilize [Luckham, Pestic. Sci., (1999) 25, 25-34].

As used herein, "micro" refers to a particle or collection of particles having diameter of from nanometers to micrometers. Microparticles, as used herein, refer to solid fenofibrate particles of irregular, non-spherical or spherical shapes with combinations of natural or synthetic phospholipids, and one or more nonionic, anionic or cationic surfactants coated or adhered onto the surfaces of the fenofibrate particles. Formulations containing these fenofibrate microparticles provide specific advantages over the unformulated, non-micronized, or "conventional" micronized particles, which include improved oral bioavailability as absorbed from the GI tract.

DESCRIPTION OF THE INVENTION

The present invention focuses on preparing submicron to micron size fenofibrate particles using a combination of surface modifier(s) with a phospholipid, and how the growth of particle size, and hence storage stability, is controlled by adding a combination of surface modifier(s) with a phospholipid to the formulation.

The use of a surface modifier or combination of surface modifiers in addition to a phospholipid is characterized by its ability to result in volume weighted mean particle size values that are (i) approximately 50% smaller than what can be achieved using phospholipid alone without the use of a surfactant with the same energy input, and (ii) provide compositions resistant to particle size growth on storage. While resistance to particle size growth on storage was an objective of this invention we were surprised to observe a significant reduction in particle size with the addition of the surfactant. In order to achieve the advantages of the present invention it is necessary that the phospholipid and the surfactant both be present at the time of particle size reduction or precipitation.

Another aspect of the present invention includes free-flowing powders of fenofibrate as well as solid dosage forms of these powders, for instance in the form of compressed tablets and the like. Surprisingly we have found that microparticulate formulations exhibit enhanced stability and bioavailability as illustrated in the data that follows.

Although we do not wish to be bound by any particular theory, it appears that these surface modifiers, that is phospholipids and one or more surfactants, absorb to the surfaces of fenofibrate, and modify the surfaces to allow smaller particle formation and stailize the formed micoparticles. The concentrations of surface modifiers used in the process described here are normally above their critical micelle contrations (CMC) and hence facilitate the formation of sub-micron to micron particles by stablizing the particles.

Phospholipid and surface modifier(s) are adsorbed onto the fenofibrate particle surfaces in sufficient quantity to retard particle growth, reduce the initial average particle size of from 5 to 100 μm to micron and submicron size particles by one or combination of methods known in the art, such as sonication, homogenization, milling, microfluidization, precipitation or recrystallization or precipitation from supercritical fluid, and maintain sub-micron and micron size particles on subsequent storage as suspension or solid dosage form.

The concentration of phospholipid or surface modifier in the suspension or solid dosage form can be present in the range of 0.1 to 50%, preferably 0.2 to 20%, and more preferably 0.5 to 10%.

The formulations prepared by this invention may be dried, e.g., by lyophilization, fluid or spray drying, into powders, which can be resuspended or filled into capsules or converted into granules or tablets with the addition of binders and other excipients known in the art of tablet making.

The phospholipid may be any natural or synthetic phospholipid, for example phosphatidylcholine, phosphatidylethanolamine, phosphatidylserine, phosphatidylinositol, phosphatidylglycerol, phosphatidic acid, lysophospholipids, sphyngomyelin, egg or soybean phospholipid or a combination thereof. The phospholipid may be salted or desalted, hydrogenated or partially or fully hydrogenated natural, semi synthetic or synthetic. Examples of commercially available phospholipids include but are not limited to egg phospholipids P123 (Pfanstiehl), Lipoid E80 (Lipoid); and hydrogenated soy phospholipids Phospholipon 90H and 100H (Natterman) and 99% pure soy or egg phosphatidyl choline (Avanti Polar Lipids).

Examples of some suitable surface modifiers include: (a) natural surfactants such as casein, gelatin, tragacanth, waxes, enteric resins, paraffin, acacia, gelatin, cholesterol esters and triglycerides, (b) nonionic surfactants such as polyoxyethylene fatty alcohol ethers, sorbitan fatty acid esters, polyoxyethylene fatty acid esters, sorbitan esters, glycerol monostearate, polyethylene glycols, cetyl alcohol, cetostearyl alcohol, stearyl alcohol, poloxamers, polaxamines, methylcellulose, hydroxycellulose, hydroxy propylcellulose, hydroxy propylmethylcellulose, noncrystalline cellulose, polyvinyl alcohol, polyvinylpyrrolidone, and synthetic phospholipids, (c) anionic surfactants such as potassium laurate, triethanolamine stearate, sodium lauryl sulfate, alkyl polyoxyethylene sulfates, sodium alginate, dioctyl sodium sulfosuccinate, negatively charged phospholipids (phosphatidyl glycerol, phosphatidyl inositol, phosphatidylserine, phosphatidic acid and their salts), and negatively charged glyceryl esters, sodium carboxymethylcellulose, and calcium carboxymethylcellulose, (d) cationic surfactants such as quaternary ammonium compounds, benzalkonium chloride, cetyltrimethylammonium bromide, chitosans and lauryldimethylbenzylammonium chloride, (e) colloidal clays such as bentonite and veegum or a combination thereof. A detailed description of these surfactants may be found in Remington's Pharmaceutical Sciences, and Theory and Practice of Industrial Pharmacy, Lachman et al, 1986.

More specifically, examples of suitable surface modifiers include one or combination of the following surfactants: polaxomers, such as Pluronic™ F68, F108 and F127, which are block copolymers of ethylene oxide and propylene oxide available from BASF, and poloxamines, such as Tetronic™ 908 (T908), which is a tetrafunctional block copolymer derived from sequential addition of ethylene oxide and propylene oxide to ethylene-diamine available from BASF, Triton™ X-200, which is an alkyl aryl polyether sulfonate, available from Rohm and Haas. Tween 20, 40, 60 and 80, which are polyoxyethylene sorbitan fatty acid esters, available from ICI Specialty Chemicals, polyoxyethylene stearate (Myrj 52) available from ICI Specialty Chemicals, Carbowax™ 3550 and 934, which are polyethylene glycols available from Union Carbide, hydroxy propylmethylcellulose, dimyristoyl phosphatidylglycerol sodium salt, sodium dodecylsulfate, sodium deoxycholate, and cetyltrimethylammonium bromide. In some cases preferably at least two surfactants are used. In a preferred aspect of the invention, when free-flowing formulations are desired, the surfactant(s) will itself be a powder.

It is thought that some of the functions of the second surface modifier(s) as they relate to this invention are (a) allowing the formation of microparticles that are about 50% smaller than the size of microparticles produced with phospholipid alone; (b) suppressing the process of Ostwald Ripening and therefore maintaining the particle size; (c) increasing the storage stability, minimizing sedimentation, and decreasing the particle growth during lyophilization and reconstitution; (d) adhering or coating firmly onto the surfaces of water-insoluble drug particles and therefore modifying the interfaces between the particles and the liquid in the resulting formulations; (e) increasing the compatibility between water-insoluble drug particles and the liquid; and (f) possibly orienting themselves preferentially with the hydrophilic portion sticking into the aqueous solution and the lipophilic portion strongly adsorbed at the water-insoluble drug particle surfaces.

The most advantageous surface active agent for fenofibrate is illustrated in the examples that follow and/or as will be apparent following empirical tests to identify the surfactant or surfactant system/combination resulting in the requisite particle size and particle size stability on storage over time.

Various procedures can be used to produce these stable micron and sub-micron size fenofibrate particles including mixing the fenofibrate with phospholipid and surfactant(s) followed by sonication, milling, homogenization, microfluidization; or precipitating from a solution of the substance using antisolvent and solvent precipitation in the presence of the phospholipid and surfactant(s). Mannitol and other agents may be added to adjust the final formulation to isotonicity as well as acting as a stabilizing aid during drying.

Unless otherwise specified, all parts and percentages reported herein are weight per unit volume (w/v), in which the volume in the denominator represents the total volume of the system. Diameters of dimensions are given in millimeters (mm=$10^{-3}$ meters), micrometers (μm=$10^{-6}$ meters), nanometers (nm=$10^{-9}$ meters) or Angstrom units (=0.1 nm). Volumes are given in liters (L), milliliters (mL=$10^{-3}$ L) and microliters (μL=$10^{-6}$ L). Dilutions are by volume. All temperatures are reported in degrees Celsius. The compositions of the invention can comprise, consist essentially of or consist of the materials set forth and the process or method can comprise, consist essentially of or consist of the steps set forth with such materials. The following examples further explain and illustrate the invention:

The following microparticle-fenofibrate formulations were prepared either by using Microfluidizer® model 110EH (Microfluidics Corp., Newton, Mass.) or Avestin model C5 (Ottawa, Canada).

A premix of the formulation was prepared by placing the ingredients in an appropriate size vessel with the required amount of water and mixed with a hand held homogenizer. The premix so formed was then placed in the inlet reservoir of the homogenizer and passing the outlet flow through a thermostatically controlled cooler to control the inlet temperature. The premix was then pumped through the homogenizer at 18,000-20,000 psi. The homogenization process can either be done by discrete passes or in continuous mode. For the sake of comparison, all formulations (except Example 2) were homogenized for 90 passes in Avestin homogenizer. The formulation in example 2 was prepared in a Microfluidizer® with using approximately 50 passes at full pressure. The formulations were harvested and particle size and other parameters measured. The particle size determination was performed with Malvern Mastersizer model Micro-Plus (Southborough, Mass.). The particle size data are presented as volume weighted mean particle size.

The composition and concentration of excipients of various microparticle fenofibrate formulations are listed below. The amount of excipients used is expressed as percent (w/w):

| Example 1 | |
|---|---|
| Fenofibrate | 10.0 |
| Phospholipon 100 H | 2.0 |
| Tween 80 | 2.0 |
| Mannitol | 5.5 |
| Mean particle size: | 0.85 μm |
| Example 2 | |
| Fenofibrate | 10.0 |
| Phospholipon 100 H | 2.0 |
| Tween 80 | 2.0 |
| Mannitol | 10.0 |
| Mean particle size: | 1.02 μm |
| Example 3 | |
| Fenofibrate | 10.0 |
| Phospholipon 100 H | 2.0 |
| PVP 30 | 1.5 |
| Mannitol | 5.5 |
| Mean particle size: | 1.28 μm |
| Example 4 | |
| Fenofibrate | 10.0 |
| Phospholipon 100 H | 2.0 |
| Myrj 52 | 1.5 |
| Mannitol | 5.5 |
| Mean particle size: | 1.21 μm |
| Example 5 | |
| Fenofibrate | 10.0 |
| Phospholipon 100 H | 2.0 |
| Poloxamer 188 | 1.5 |
| Mannitol | 5.5 |
| Mean particle size: | 1.12 μm |

EXAMPLE A

For the purpose of comparison (not according to the invention) using only a phospholipid, (without the second surface modifier, Tween 80), fenofibrate particles were also prepared using the same procedure as Example 1:

| | |
|---|---|
| Fenofibrate | 10.0 |
| Phospholipon 100 H | 2.0 |
| Mannitol | 5.5 |
| Mean particle size: | 3.17 μm |

A comparison of the resulting mean particles size of the final formulations in Examples 1 to 5, inclusive, with Example A demonstrate the effect of adding the second surface modifier on the final particle size. Also, it was observed that the use of a second surface modifier helps to eliminate the thick slurry produced when Phospholipon 100H is used alone as in Example A.

EXAMPLE 6

Oral Bioavailability of Fenofibrate Microparticles in Human Subjects.

The Fenofibrate composition used in Example 2 was tested in a human volunteers study. The study consisted of oral administration of the fenofibrate formulation to eight human volunteers in a single dose crossover design, using the marketed formulation as a reference. The dose administered was 67 mg. Blood samples were collected before and after each administration at various time points over 120 hours.

The drug concentration in blood samples was determined by high-pressure liquid chromatography by monitoring for the level of the metabolite, fenofibric acid. The pharmacokinetic results are presented in Table 1 and demonstrate the superior bioavailability of the fenofibrate formulation over the commercially available product.

TABLE 1

$C_{max}$ and $AUC_{0}$-inf for Fenofibric Acid

| | $C_{max}$ (ng.ml$^{-1}$) | $AUC_{0-inf}$ (ng.ml$^{-1}$.h) |
|---|---|---|
| Fenofibrate microparticles (67 mg) | 2528 | 57235 |
| Commercially available fenofibrate (67 mg) product | 1372 | 38629 |
| Dunnett's t-test (log transformed data) | $p < 0.05$ | $p < 0.05$ |

What is claimed is:

1. A method of preparing fenofibrate microparticles, comprising the steps of:
   (1) mixing the fenofibrate particles with (a) a natural or synthetic phospholipid and (b) at least one non-ionic, anionic, or cationic surfactant to form a mixture, prior to or during a reduction of particle size, said mixture comprising an alkyl aryl polyether sulfonate, a sorbitan fatty acid ester, a polyoxyethylene sorbitan fatty acid ester, a polyoxyethylene stearate, a polyethylene glycol, benzalkonium chloride, cetyltrimethylammonium bromide, lauryldimethylbenzylammonium chloride, or a combination of any thereof; and
   (2) subjecting the mixture of step (1) to size reduction by an energy input procedure selected from one or more of sonication, milling, homogenization, microfluidization, or precipitation from solution using antisolvent and solvent precipitation in the presence of the mixture to produce fenofibrate microparticles having a volume-weighted mean particle size that is about 50% smaller than particles produced without the presence of the surfactant using the same energy input procedure.

2. A method of preparing fenofibrate microparticles, comprising the steps of:
   (1) mixing the fenofibrate particles with (a) a natural or synthetic phospholipid selected from the group consisting of phosphatidyicholine, phosphatidylethanolamine, phosphatidylserine, phosphatidylinositol, phosphatidyiglycerol, sphingomyelin, dimyristoyl phosphatidyiglycerol sodium salt, phosphatidic acid, lysophospholipids and combinations thereof, and (b) at least one non-ionic, anionic, or cationic surfactant to form a mixture, prior to or during a reduction of particle size; and
   (2) subjecting the mixture of step (1) to size reduction by an energy input procedure selected from one or more of sonication, milling, homogenization, microfluidization, or precipitation from solution using antisolvent and solvent precipitation in the presence of the mixture to produce fenofibrate microparticles having a volume-weighted mean particle size that is about 50% smaller than particles produced without the presence of the surfactant using the same energy input procedure.

3. A method of preparing fenofibrate microparticles, comprising the steps of:
   (1) mixing the fenofibrate particles with (a) a natural or synthetic phospholipid and (b) at least one non-ionic, anionic, or cationic surfactant to form a mixture, prior to or during a reduction of particle size; and
   (2) subjecting the mixture of step (1) to size reduction by an energy input procedure selected from one or more of sonication, milling, homogenization, microfluidization, or precipitation from solution using antisolvent and solvent precipitation in the presence of the mixture to produce fenofibrate microparticles, wherein the fenofibrate microparticles are 5-100 μm in size, said fenofibrate microparticles having a volume-weighted mean particle size value that is about 80% smaller than particles produced without the presence of the surfactant using the same energy input procedure.

4. A method of preparing fenofibrate microparticles, comprising the steps of:
   (1) mixing the fenofibrate particles with (a) a natural or synthetic phospholipid and (b) at least one non-ionic, anionic or cationic surfactant to form a mixture, prior to or during a reduction of particle size, wherein the mixture comprises the surfactant in a concentration above its critical micelle concentration; and thereafter
   (2) subjecting the mixture of step (1) to size reduction by an energy input procedure selected from one or more of sonication, milling, homogenization, microfluidization, or precipitation from solution using antisolvent and solvent precipitation in the presence of the mixture to produce fenofibrate microparticles having a volume-weighted mean particle size that is about 50% smaller than particles produced without the presence of the surfactant using the same energy input procedure.

5. The method according to any one of claims 1, 2, 3, or 4, wherein step (1) further comprises: mixing the fenofibrate particles with (a) at least two phospholipids and at least one surfactant, (b) a phospholipid and at least two surfactants, or (c) at least two phospholipids and at least two surfactants.

6. The method according to any one of claims 1, 2, 3, or 4, wherein the method comprises preparing a pharmaceutically acceptable composition from the composition of fenofibrate microparticles.

7. The method according to claim 6, wherein the method comprises preparing a suspension of the fenofibrate microparticles.

8. The method according to claim 6, wherein the method comprises preparing a powder from the composition by lyophilization, fluid drying, or spray drying.

9. The method according to claim 8, wherein the method comprises preparing an orally administrable gel capsule comprising the powder.

10. The method according to claim 8, wherein the method comprises preparing an orally administrable granule from the powder.

11. The method according to claim 8, wherein the method comprises preparing an orally administrable tablet comprising the powder.

12. The method according to claim 6, wherein the composition is spray dried and the surfactant consists of polyvinylpyrrolidone, or a combination of polyvinylpyrrolidone and one or more additional surfactants.

13. The method according to claim 12, wherein the composition is further converted into granules.

14. A composition comprising fenofibrate microparticles produced by the method according to any one of claims 1, 2, 3, or 4.

15. A pharmaceutically acceptable composition comprising granules produced by the method according to claim 13.

16. The method according to any one of claims 1, 2, 3, or 4, wherein the surfactant is selected from the group consisting of casein, tragacanth, enteric resins, cholesterol esters, polyoxyethylene fatty alcohol ethers, polyoxyethylene fatty acid esters, sorbitan esters, glycerol monostearate, polyethylene glycols, cetyl alcohol, cetostearyl alcohol, stearyl alcohol, poloxamers, polaxamines, polyvinyl alcohol, polyvinylpyrrolidone, potassium laurate, triethanolamine stearate, sodium lauryl sulfate, alkyl polyoxyethylene sulfates, sodium alginate, dioctyl sodium sulfosuccinate, negatively-charged glycerol esters, quaternary ammonium compounds, chitosans, colloidal clays, sodium dodecylsulfate, sodium deoxycholate, and combinations thereof.

17. A method of preparing fenofibrate microparticles comprising the steps of:
   (1) mixing the fenofibrate particles with (a) a natural or synthetic phospholipid and (b) at least one non-ionic, anionic or cationic surfactant to form a mixture, prior to or during a reduction of particle size, said surfactant being selected from one or more of casein, tragacanth, enteric resins, cholesterol esters, polyoxyethylene fatty alcohol ethers, polyoxyethylene fatty acid esters, sorbitan esters, glycerol monostearate, polyethylene glycols, cetyl alcohol, cetostearyl alcohol, stearyl alcohol, poloxamers, polaxamines, polyvinyl alcohol, polyvinylpyrrolidone, potassium laurate, triethanolamine stearate, sodium lauryl sulfate, alkyl polyoxyethylene sulfates, sodium alginate, dioctyl sodium sulfosuccinate, negatively-charged glycerol esters, quaternary ammonium compounds, chitosans, colloidal clays, sodium dodecylsulfate, sodium deoxycholate, and combinations thereof, and (2) subjecting the mixture of step (1) to size reduction by an energy input procedure selected from one or more of sonication, milling, homogenization, microfluidization, or precipitation from solution using antisolvent and solvent precipitation in the presence of the mixture to produce fenofibrate microparticles having a volume-weighted mean particle size that is about 50% smaller than particles produced without the presence of the surfactant using the same energy input procedure.

18. The method according to claim 17, wherein step (1) further comprises: mixing the fenofibrate particles with (a) at least two phospholipids and at least one surfactant, (b) a phospholipid and at least two surfactants, or (c) at least two phospholipids and at least two surfactants.

19. The method according to claim 17, wherein the mixture comprises an alkyl aryl polyether sulfonate, a sorbitan fatty acid ester, a polyoxyethylene sorbitan fatty acid ester, a polyoxyethylene stearate, a polyethylene glycol, benzalkonium chloride, cetyltrimethylammonium bromide, lauryldimethylbenzylammonium chloride, or a combination of any thereof.

20. The method according to claim 17, wherein the phospholipid is selected from the group consisting of phosphatidylcholine, phosphatidylethanolamine, phosphatidylserine, phosphatidylinositol, phosphatidylglycerol, sphingomyelin, dimyristoyl phosphatidylglycerol sodium salt, phosphatidic acid, lysophospholipids and combinations thereof.

21. The method according to claim 17, wherein the fenofibrate microparticles are 5-100 μm in size, said fenofibrate microparticles having a volume-weighted mean particle size value that is about 80% smaller than particles produced without the presence of the surfactant using the same energy input.

22. The method according to claim 17, wherein the mixture comprises a surfactant in a concentration above its critical micelle concentration.

23. The method according to claim 17, wherein the method comprises preparing a pharmaceutically acceptable composition from the composition of fenofibrate microparticles.

24. The method according to claim 23, wherein the method comprises preparing a suspension of the fenofibrate microparticles.

25. The method according to claim 23, wherein the method comprises preparing a powder from the composition by lyophilization, fluid drying, or spray drying.

26. The method according to claim 25, wherein the method comprises preparing an orally administrable tablet comprising the powder.

27. The method according to claim 23, wherein the composition is spray dried and the surfactant consists of polyvinylpyrrolidone, or a combination of polyvinylpyrrolidone and one or more additional surfactants.

28. The method according to claim 27, wherein the composition is further converted into granules.

29. A pharmaceutically acceptable composition comprising granules produced by the method according to claim 28.

* * * * *